(12) United States Patent
Ding et al.

(10) Patent No.: US 7,226,617 B2
(45) Date of Patent: Jun. 5, 2007

(54) THERMOSENSITIVE AND BIODEGRADABLE MICROGEL AND A METHOD FOR THE PREPARATION THEREOF

(75) Inventors: Jiandong Ding, Shanghai (CN); Wen Zhu, Shanghai (CN); Biaobing Wang, Shanghai (CN); Ying Zhang, Shanghai (CN)

(73) Assignee: Fudan University, Shunghai (CN)

( * ) Notice: Subject to any disclaimer, the term of this patent is extended or adjusted under 35 U.S.C. 154(b) by 382 days.

(21) Appl. No.: 10/762,029

(22) Filed: Jan. 20, 2004

(65) Prior Publication Data

US 2004/0156906 A1 Aug. 12, 2004

(30) Foreign Application Priority Data

Feb. 8, 2003 (CN) ................................ 03 1 15319

(51) Int. Cl.
A61K 9/14 (2006.01)
(52) U.S. Cl. ...................... 424/486; 424/426; 424/489; 424/501
(58) Field of Classification Search .................. 525/90; 522/71; 424/486, 426, 489
See application file for complete search history.

(56) References Cited

U.S. PATENT DOCUMENTS

| 4,352,883 | A | | 10/1982 | Lim ........................... 435/178 |
| 4,716,203 | A | | 12/1987 | Casey et al. ................. 525/408 |
| 5,739,210 | A | * | 4/1998 | Scranton et al. ............. 525/279 |
| 5,986,043 | A | | 11/1999 | Hubbell et al. .............. 528/354 |
| 6,030,634 | A | | 2/2000 | Wu et al. .................... 424/423 |
| 6,060,582 | A | | 5/2000 | Hubbell et al. .............. 528/354 |
| 6,129,761 | A | | 10/2000 | Hubbell et al. ................ 623/11 |
| 6,201,065 | B1 | * | 3/2001 | Pathak et al. .................. 525/90 |
| 6,306,922 | B1 | * | 10/2001 | Hubbell et al. ................ 522/71 |
| 6,541,033 | B1 | | 4/2003 | Shah ........................... 424/486 |
| 2003/0099709 | A1 | | 5/2003 | Shah et al. .................. 424/469 |

OTHER PUBLICATIONS

Hirose et al., Macromolecules 1987, vol. 20, 1342-1344.*
Dowding et al. (Journal of Colloid and Interface Science 2000, 221, 268-272).*
Baldwin S P., Saltzman W M., "Materials for Protein Delivery in Tissue Engineering," Adv. Drug. Deliv. Rev. 33: 71-86 (1998).
Blanco D., Alonso M J., "Protein Encapsulation and Release from Poly(lactide-co-glycolide) Microspheres: Effect of the Protein and Polymer Properties and of the Co-encapsulation of Surfactants," Eur. J.Pharm. Biopharm. 45: 285-294 (1998).
Bromberg L E., Ron E S., "Temperature-responsive Gels and Thermogelling Polymeric Matrices for Protein and Peptide Delivery," Adv. Drug. Deliv. Rev. 31: 197-221 (1998).
Cho K Y., Choi S H., Kim C H., Nam Y S., Park T G.., Park J K., "Protein Release Microparticles Based on the Blend of Poly(d,l-lactic-co-glycolic acid) and Oligo-ethylene glycol Grafted Poly(l-lactide)," J. Control. Release 76: 275-284 (2001).
Cohen S., Yoshioka T., Lucarelli M., Hwang L H., Langer R., "Controlled Delivery Systems for Proteins Based on Poly(lactic/glycolic acid) Microspheres," Pharm. Res. 8: 713-720 (1991).
Fu J., Zhou R X., Fan C L., "Studies on the Syntheses and Properties of Poly(ester-anhydride)s for DDS," Chemical Journal of Chinese Universities 19(5): 813-816 (1998).
Fu J., Zhou R X., Fan C L., "Studies on the Syntheses and Drug Release Properties of Polyanhydrides Containing Phosphonoformic (or Acetic) Acid Ethyl Ester in the Main Chain," Chemical Journal of Chinese Universities 18(10): 1706-1710 (1997).
Jain R A., Rhodes C T., Railkar A M., Malick A W., Shal N H., "Controlled Release of Drugs from Injectable in Situ Formed Biodegradable PLGA Microspheres: Effect of Various Formulation Variables," Eur. J. Pharm. Biopharm. 50: 257-262 (2000).
Jeong B., Bae Y H., Lee D S., Kim S W., "Biodegradable Block Copolymers as Injectable Drug-delivery Systems," Nature 388: 860-862 (1997).
Langer R., "Drug Delivery and Targeting," Nature 392: 5-10 (1998).
Lanza R P., Langer R., Vacanti J., Principles of Tissue Engineering (2nd Ed.), Academic Press, New York, 2000.
Li M X., Zhuo R X., Qu F Q., "Synthesis and Characterization of Novel Biodegradable Poly(ester amide) with Ether Linkage in the Backbone Chain," J. Polym. Sci. part A: Polym. Chem. 40(24): 4550-4555 (2002).
Sawhney A S., Hubbell J A., "Rapidly Degraded Teroplymers of dl-lactide, glycolide, ande—caprolactone with Increased Hydrophilicity and Copolymerization with Polyethers," J. Biomed. Mater. Res. 24(10): 1397-1411 (1990).
Sawhney A S., Pathak C P., Hubbell J A., "Bioerodible Hydrogels Based on Photopolymerized Poly(ethyleneglycol)-co-poly(α-hydroxy acid) Diacrylate Macromers," Macromolecules 26: 581-587 (1993).
Singh M., Shirley B., Bajwa K., Samara E.□Hora M., O'Hagan D., "Controlled Release of Recombinant Insulin-like Growth Factor from a Novel Formulation of Polylactide-co-glycolide Microparticles," J. Control. Release 70: 21-28 (2001).

(Continued)

*Primary Examiner*—Michael G. Hartley
*Assistant Examiner*—James W. Rogers
(74) *Attorney, Agent, or Firm*—Morgan & Finnegan, LLP

(57) ABSTRACT

The present invention provides a thermosensitive and biodegradable microgel and a method of synthesizing such microgels. The thermosensitive and biodegradable microgel is synthesized from a macromer comprising a thermosensitive block polymer co-polymerized with a biodegradable moiety encapped with a cross-linkable or polymerizable moiety at either end. The microgels of the present invention are synthesized by inverse suspension polymerization of the macromers. The microgels are biodegradable into components that are non-toxic and easily removed from the body. The microgel of the present invention is temperature sensitive and is "intelligent" as well as biodegradable. The microgels are preferably used for the controlled release of a drug or in tissue engineering. Most preferably, the microgels are suitable for the control release of biologically active substances such as proteins.

9 Claims, 4 Drawing Sheets

OTHER PUBLICATIONS

Wu C., Zhou S Q., "Thermodynamically Stable Globule State of a Single Poly(N-isopropylacrylamide) Chain in Water," Macromolecules 28(15): 5388-5390 (1995).

Wu C., Zhou S Q., "Internal Motions of Both Poly(N-isopropylacrylamide) Linear Chains and Spherical Microgel Particles in Water," Macromolecules 29(5):1574-1578 (1996).

Yasuhiko T., "The Importance of Drug Delivery Systems in Tissue Engineering," Pharmaceutical Science & Technology Today 3: 80-89 (2000).

Zentner G M., Rathi R., Shin C., McRea J C., Seo M H., Oh H., Rhee B G., Mestecky J., Moldoveanu Z., Morgan M., and Weitman S., "Biodegradable Block Copolymers for Delivery of Proteins and Water-insoluble Drugs," J. Control. Release 72: 203-215 (2001).

Zhuo R X., Li W., "Preparation and Characterization of Macroporous Poly(N-isopropylacrylamide) Hydrogels for the Controlled Release of Proteins," J. Polym. Sci. part A: Polym. Chem. 41(1): 152-159 (2003).

Zhu Z X., Xiong C D., Zhang L L., Yuan M L., Deng X M., "Preparation of Biodegradable Polylactide-co-poly(ethylene glycol) Copolymer by Lactide Reacted Poly(ethylene glycol)", Eur. Polym. J. 35: 1821-1828 (1999).

* cited by examiner (a)                               (b)

Crosslinked chemical bonds $F(DC)_2$    Chain between the crosslinked bonds

F    A temperature sensitive polymer or oligomer

D    A biodegradable moiety

C*    A cross-linkable moiety

C    A cross-linking moiety

THERMOSENSITIVE AND BIODEGRADABLE MICROGEL AND A METHOD FOR THE PREPARATION THEREOF

FIELD OF THE INVENTION

The present invention relates to a polymeric biodegradable material that is suitable for use in a pharmaceutical formulation. More particularly, it is directed to a thermosensitive and biodegradable microgel, a method of preparation of the biodegradable microgel and a unique application of the material.

BACKGROUND OF THE INVENTION

Controlled Release of Recombinant Proteins

With the rapid advances made in biotechnology and genetic engineering, a growing number of proteins and peptides have been produced by recombinant DNA technology for use as pharmaceutical therapeutic agents. Such proteins include erythropoietin (EPO), granulocyte-colony-stimulating factor (G-CSF and GM-CSF), interferons (alpha, beta, gamma, and consensus), insulin and interleukin-1 etc. In addition to these proteins, several hundred other proteins are currently undergoing clinical trials as drugs. Because proteins have generally short in vivo half-lives and negligible oral bioavailability, they are typically administered by frequent injection, a procedure that is hard to accept for most patients. It has been conjectured that the employment of controlled release technology for the administration of such therapeutic agents can alleviate such a problem to a degree. Hence, it is highly desirable to develop sustained-release systems.

Tissue engineering is another area of biomedical research that is much pursued. The goal of tissue engineering is to employ the techniques of modern biotechnology to regenerate or replace lost or damaged tissues and organs. In addition to cells and their scaffolds, a class of proteins called growth factors are frequently required for tissue engineering. These include nerve growth factor (NGF), platelet-derived growth factor (PDGF), fibroblast growth factor (FGF), epidermal growth factor (EGF), tumor necrosis factor (TNF) etc. Growth factors, most of which are globular, are effective in the process for supplying the oxygen and nutrients which are necessary for the survival of the transplanted cells in organ transplants (Lanza et al., 2000).

Cell growth factors are usually injected locally and active targeting of the agent is not absolutely necessary. However, it has been found that direct single-time injection of a growth factor solution into a regeneration site is less effective, as the injected growth factor rapidly diffuses away from the site. Repeated injection is, of course, inconvenient. Novel drug delivery systems are thus desired. The projection is that controlled delivery systems for recombinant proteins will be a major technology in tissue engineering during the next century. (Yasuhiko, (2000) *Pharmaceutical Science & Technology Today*, 3: 80–89)

Microparticles as Controlled-release Carriers

Microparticles has held promises in many areas of medicine. In recent years, microparticles have garnered growing attention and have been the subject of investigation as an ideal drug carrier. Up to the present, microparticles have found application in more than thirty different drugs, including antipyretic analgesic, antibiotic, fibrin and anticancer drugs, etc. Biomolecules such as proteins, enzymes, hormones and peptides, are sensitive and easily degraded. The most promising controlled-release approach would be to encapsulate such materials within microparticles. A principal advantage of formulating these sensitive biomolecules in microparticles is that they may be administrated by injection, and does not require formal surgical procedure for their administration.

Materials that are useful for making into microparticles can be grouped into three categories: natural polymers such as glutin, alginate and chitosan; semisynthetic polymers such as carboxymethyl cellulose, cellulose acetate phthalate, methyl cellulose and ethyl cellulose; and synthetic polymers such as polyamide, poly(acrylic acid), poly(vinyl alcohol), polycarbonate, poly(amino acid), poly(lactic acid), poly(lactide-co-glycolide) and poly(d,l-lactide)-poly(ethylene glycol) copolymer. Natural polymers are abundant and usually biodegradable. However, the principal disadvantage is in the difficulty of their modification and purification. There are significant batch to batch and source to source variations, due to the need to isolate these materials from living organisms.

The requirements for materials used for encapsulation are suitable drug release rates, stability, non-toxicity, absence of interference with the pharmacological action, strength, suitable hydrophilicity, plasticity, permeability and solubility. In addition, it would be desirable to have microparticles made from biodegradable polymers to eliminate the need for their removal after the agent has been released. Synthetic polymers are available in a wide range of compositions with readily adjustable properties. Therefore, much attention has been paid to the use of biodegradable materials. Synthetic polyesters have, especially, been widely investigated. See, Blanco et al., (1998) *Eur. J. Pharm. Biopharm.* 45: 285–294, Zhu et al., (1999) *Eur. Polym. J.* 35: 1821–1828.

Up to the present, most researchers have concentrated on the use of hydrophobic biodegradable polymers. Singh et al., (2001) *J Control. Release* 70: 21–28, reported the in vitro and in vivo release behavior of polylactide-co-glycolide microparticles with entrapped insulin growth factor (rhIGF-I). Jain et al., (2000) *Eur. J. Pharm. Biopharm*, 50: 257–262, investigated the release behavior of bovine heart cytochrome C and heart skeletal muscle myoglobin from injectable PLGA microparticles.

There are various problems associated with the applications of such polymers. The problems are: the difficulty of the homogeneous dispersal of the hydrophilic drug within the polymer matrices, the inability of certain macromolecules to diffuse out through the polymer matrix, the unpredictability of drug release behavior, the deterioration of the drug, e.g., denaturation caused by the presence of organic solvents, and irritation to the organism due to side effects caused by the presence of organic solvents.

Degradable polymers containing water-soluble polymers have also been investigated. Copolymerization of lactide, glycolide and caprolactone with the polyether such as poly-ethylene glycol (PEG) was expected to partially overcome the above drawbacks, while taking advantage of the virtues of both biodegradable and hydrophilic polymers. Sawhney et al., (1990) *J Biomed. Mater. Res*, 24(10): 1397–1411, Casey et al., (U.S. Pat. No. 4,716,203) describes the synthesis of a block copolymer of PGA (poly(glycolic acid)) and PEG. Cho et al (2001) *J. Control. Release* 76: 275–284, applied the W/O/W double emulsion method to prepare PLLA-PEG copolymer microparticles, where bovine serum albumin (BSA) was used as the model drug. Although the copolymers have improved hydrophilicity, most of the biodegradable synthetic polymers reported so far can only be processed in organic solvents which are harmful to protein activity. For these reasons, it is desirable to have a hydrogel as a preferable candidate as a protein drug carrier.

Use of Hydrogel as Protein Carriers

Hydrogels have been intensely investigated as protein drug vehicles because of their excellent biocompatibility and hydrophilicity. Compared with other synthetic biomaterials such as PLGA, hydrogels more closely resemble natural living tissues because of their high water contents and soft and rubbery consistency. The nature of hydrogels minimizes irritation to surrounding tissues. Furthermore, hydrogels are useful in protecting the drug from hostile environments, e.g., the presence of enzymes or the low pH in the stomach. Some biodegradable hydrogels have been reported, Sawhney et al., (1993) *Macromolecules*, 26:581–587, and Hubbell et al., U.S. Pat. Nos. 5,986,043, 6,060,582, and 6,306,922. However, the hydrogels were synthesized via ultraviolet polymerization or photopolymerization, which are not suitable for entrapping ultraviolet-sensitive proteins.

There are many different physical forms of hydrogels, such as microgel, bulk gel etc. Since microparticles are injectable, microgel would be a good carrier for proteins. Drug delivery systems in the form of microparticles may enable the release of the therapeutic agent in a specified area or over a specified time period. Kim S W et al., (1997) *Nature* 388: 860–862, studied injectable hydrogel. During the process of loading drug, the use of any organic solvent which can denature the protein was avoided. However, in this case, bulk gels instead of gel particles were used, and the encapsulation temperature was higher than human body temperature.

Cross-linked glutin and collagen have also been employed as a hydrogel to encapsulate peptides of opposite charges. Alginates have been shown to be able to encapsulate biological materials. Lim, U.S. Pat. No. 4,352,883. But the rates of degradation of both kinds of gels were not easily controlled over a wide range of conditions.

In addition to swelling, some hydrogels also show changes in response to stimuli. The present inventors explored these characteristics for developing novel ways for drug loading and drug release.

There have been many studies on materials for drug release. These materials are either merely biodegradable as reported by Cohen et al., (1991) *Pharm. Res.*, 8: 713–720, Langer et al., (1998) *Nature* 392: 5–10, Bawa et al., (1985) *J. Control. Release*, 1: 259–267, Li et al., (2002) *J. Polym. Sci. part A: Polym. Chem.* 40(24): 4550–4555, Fu J. et al., (1997, 1998) *Chemical Journal of Chinese Universities*, 18(10):1706–1710,19(5):813–816; or merely responsive to environmental stimuli, see e.g, Wu et al., (1995, 1996) *Macromolecules* 28(15): 5388–5390, 29(5):1574–1578, Wu, U.S. Pat. No. 6,030,634; Zhou et al., (2003) *J. Polym. Sci. part A: Polym. Chem.* 41(1):152–159. There have been a few reports about a material having a combination of both properties, Shah, U.S. Pat. No. 6,541,033, and Shah et al., U.S. Pat. No. 0,099,709. From these few reports, the use of biodegradable and thermosensitive microgels in a drug delivery system is still quite limited.

RealGel™ is a block copolymer with temperature-sensitivity and degradability, Zentner et al., (2001) *J. Control. Release*, 72: 203–215. It is not a chemical gel but a physical gel. The term of "chemical gel" represents a gel in which gellation is due to chemical crosslinking, while the term of "physical gel" denotes a gel in which gellation is induced by physical parameter such as temperature. In addition, this gel is a liquid at high temperature, and forms a semi-solid gel when it can be used to encapsulate a drug at a lower temperature. However, the positive temperature sensitivity may lead to denaturation of the protein when it is being encapsulated at a high temperature before gelation. A negative temperature sensitive biodegradable chemical hydrogel has been reported by Hubbell et al., (2000) U.S. Pat. No. 6,129,761, but it was a bulk gel, wherein an ultraviolet initiation method was used. There are difficulties in applying this type of bulk gel in an inverse suspension polymerization process.

In accordance with the present invention, a thermosensitive, biodegradable microgel for the sustained delivery of drugs is provided. The drug is released at a controlled rate from the microgel, which eventually biodegrade into non-toxic products. The rate of degradation can also be adjusted by adjusting the composition of the biodegradable groups.

Drug Loading

In order to encapsulate protein molecules within microparticles, most researchers utilize a solvent evaporation method because this method is useful for achieving a high level of encapsulation. There are basically two different approaches for encapsulation: a water/oil/water double emulsion or a single emulsion in which the micronized protein powder is dispersed into an organic solvent phase containing the dissolved polymer. However, many proteins are irreversibly denatured by contact with organic solvents necessary for dissolving the polymer. Thus, one of the main problems of such methods is the partial or complete loss of biological activity. There are some additives, such as albumin and polysaccharides, which can be used to stabilize the proteins to a certain degree and affect the release behavior, Baldwin et al., (1998) *Adv. Drug. Deliv. Rev.*, 33: 71–86. The alternative, but less frequently reported method is loading the proteins or peptides into a microgel by swelling the microgels in an aqueous solution and subsequent drying. However, this method provides only a low level of encapsulation efficiency. Thus, a further object of the present invention is to provide a process of manufacturing a microgel and loading a protein drug into the microgel with a relatively high loading level.

Compared to in situ encapsulation of the drug, absorption of the drug AFTER the preparation of the gel or hydrogel provides several striking advantages: (1) The biocompatibility of the polymeric material may be enhanced because gel without protein loaded can be easily cleaned to wash out any residual monomers, initiators etc.; (2) the steps of preparing the microgel followed by encapsulation of the protein are separate steps, making it much easier to control each of the two steps independently. On its face, it has been considered impractical to adsorb the proteins after the preparation of the gel or microgel. The reasoning was that if a drug can penetrate the gel easily, it would not be released slowly; whereas, if drug release can be controlled well, it would be hard to adsorb the drug into the gel after gel formation and would lead to a very low loading level.

In accordance with the present invention, the hydrogels of the present invention have been designed to be "intelligent" to overcome the difficulties encountered previously. The "intelligent" hydrogels of our invention comes from the temperature sensitivity of the polymeric material in a particular solvent media. The gel swells at a low temperature and is ready for drug absorption at this low temperature. However, the gel contracts or gelates at a higher temperature, such as the body temperature, and provides a unique way for controlling the release of the drug after injection into the body.

The object and features of the present invention will be made apparent from the following description.

SUMMARY OF THE INVENTION

In accordance with a preferred embodiment of the present invention, the patent provides a thermosensitive, biocompatible and biodegradable microgel for potential use in drug delivery and other biomedical applications such as tissue engineering. The microgel is obtained by polymerizing a macromer through inverse suspension polymerization. Suitable thermosensitive, biocompatible, polymerizable and basically water soluble macromers are disclosed herein. The term "macromer" refers to the macro-monomer which is a macromolecule or an oligomer and is itself polymerizable. The macromer according to the present invention comprises a water soluble and thermosensitive region as the core with hydrolyzable biodegradable oligomeric extensions, and free-radical-polymerizable moiety(es) at terminals.

The microgels resulting from polymerization of such macromers are particularly useful for controlled drug delivery. The pore size of the microgel is decreased greatly when the temperature is higher than its phase transition temperature, namely, the physical gellation temperature, which is preferably between 4° C. and 37° C. The chemically cross-linked microgel network is able to entrap and homogeneously disperse a protein drug throughout the network at a lower temperature, usually at 4° C., and release the protein drug at a controlled rate at a higher temperature, usually at 37° C.

Organic solvents and toxic substances can be removed completely before drug loading, and the loaded drug would not leach out from the microgel at body temperature, if the size of the drug, such as a protein drug, is between the pore sizes of microgel before and after phase transition temperature, usually between 4° C. and 37° C.; or if the entrapped substance has been held in the microgel network due to further gelation within the microgel over the phase transition temperature. In this manner, protein activity is maintained with a relatively high level of encapsulation efficiency. Drug release is also effected by diffusion of the drug and the degradation of the microgels. The rate of degradation can be controlled by custom designing the structure of the polymer or polymers used to make the microgel.

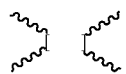

represents chemical cross-linked bonds; $F(DC)_2$ represents a microgel block co-polymer; wherein F is a temperature sensitive polymer or oligomer; D is a biodegradable moiety, such as a polyglycolide, C* is a cross-linkable moiety provided at the end of the block co-polymer chain of F and D to form a macromer, $F(DC^*)_2$, and C is a crosslinked moiety after cross-linking of the macromers $F(DC^*)_2$.

Figure 2A:
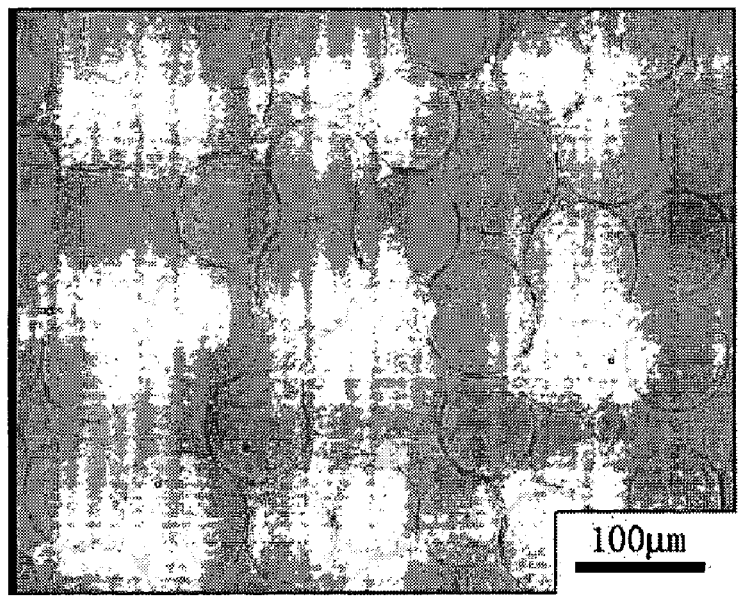

FIG. 2a shows the morphology of a microgel resulting from $(PEO_{100}\text{-}PPO_{65}\text{-}PEO_{100})\text{-}LA_8\text{-}DA$ macromers at 4° C. observed in an inverted optical microscope.

Figure 2B:
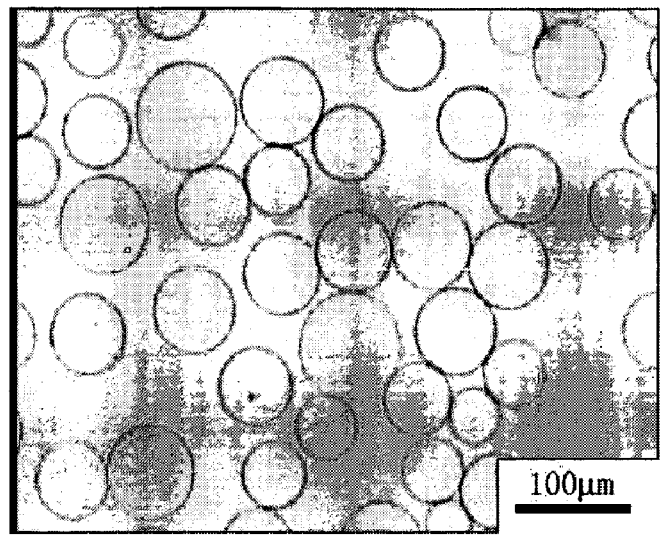

FIG. 2b shows the morphology of a microgel resulting from $(PEO_{100}\text{-}PPO_{65}\text{-}PEO_{100})\text{-}LA_8\text{-}DA$ macromers, at 37° C. observed in an inverted optical microscope.

Figure 3:
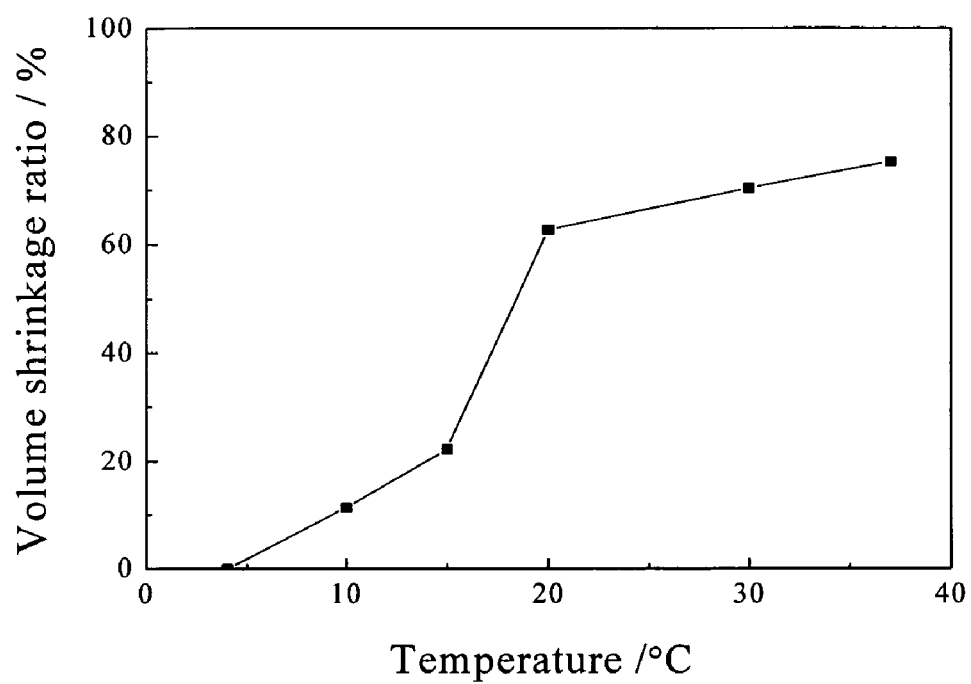

FIG. 3 shows the effect of temperature on the particle size of a microgel. The volume of each microparticle was calculated from the diameter measured using the optical micrograph.

Figure 4:
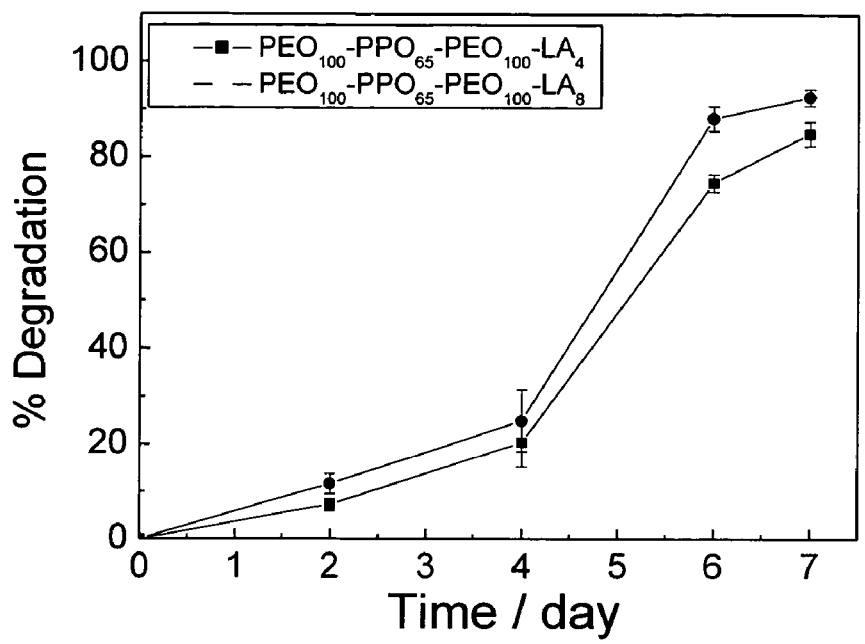

FIG. 4 shows the rate of degradation of the microgel resulting from $(PEO_{100}\text{-}PPO_{65}\text{-}PEO_{100})\text{-}LA_4\text{-}DA$ macromers and $(PEO_{100}\text{-}PPO_{65}\text{-}PEO_{100})\text{-}LA_8\text{-}DA$ macromers in PBS at 37° C.

Figure 5:
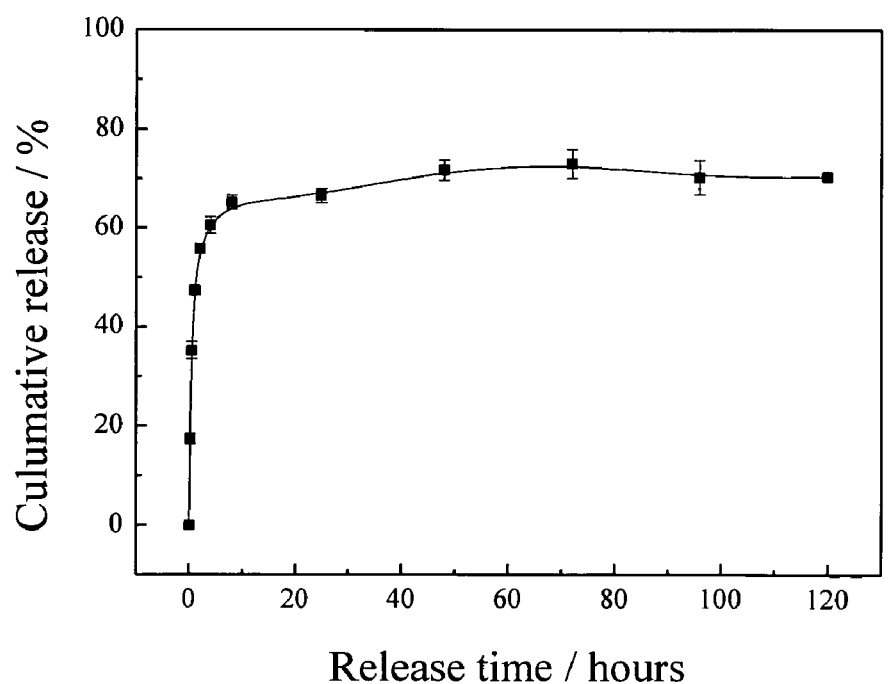

FIG. 5 shows the release of BSA from $(PEO_{100}\text{-}PPO_{65}\text{-}PEO_{100})\text{-}LA_4$ microgel into PBS at 37° C.

Figure 6:
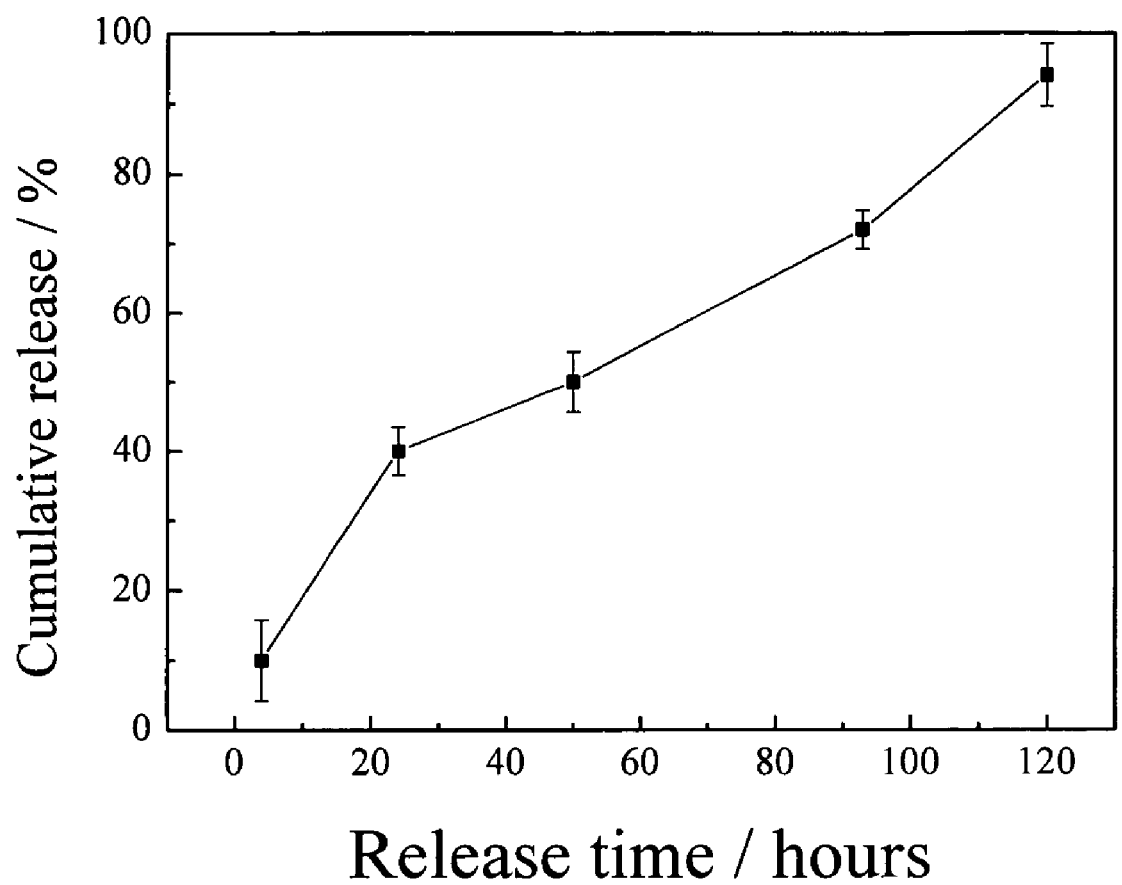

FIG. 6 shows the release of insulin from $(PEO_{100}\text{-}PPO_{65}\text{-}PEO_{100})\text{-}CL_4$ microgel into PBS at 37° C.

DETAILED DESCRIPTION OF THE INVENTION

Disclosed herein is a biodegradable and thermosensitive microgel formed via polymerization of macromers. The macromers are obtained as follows: a thermosensitive oligomer or polymer (F) polymerized with a biodegradable moiety (D), and provided with a polymerizable moiety (C*). The microgel is formed by free radical initiation in an inverse suspension polymerization process. In order to clarify the terms, "catalyst" herein denotes an additive in the chemical reaction between F and D in one of the steps in the preparation of the macromers, whereas the term "initiator" denotes an additive in the crosslinking or polymerization of the macromers to form the microgel of the present invention.

The Macromers and Microgels

The macro-monomer ("macromer") is a high molecular weight polymerizable monomer and comprises a biocompatible and thermosensitive polymer or an oligomer. (F) preferably as a central part of the system. A block copolymer comprising DFD, wherein D is a biodegradable moiety, is synthesized by a ring opening polymerization process in the presence of an aliphatic internal ester. The block copolymer formed provided with crosslinkable ends (the macromer $F(DC^*)_2$) is then crosslinked to form a microgel. The crosslinkable moiety C* may comprise a double bond end group provided at each terminus of the block copolymer DFD.

Figure 1:
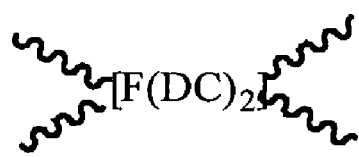
FIG. 1 schematically illustrates the internal chemical structure of the microgels in the present invention (a) and associated macromer (b), where
Figure 1:
Figure 1:
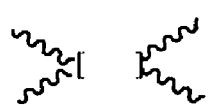

The resultant microgels are chemically cross-linked networks comprising at least one thermosensitive region and one biodegradable region. In particular, the microgel comprises a thermosensitive core region F extended at both ends by a biodegradable moiety D, and provided with a crosslinked moiety C at each terminus. The chemical structure of the microgel may be represented by the structure shown in FIG. 1.

In addition to a thermosensitive region, a biodegradable component and two cross-linkable moieties at two ends, the block copolymer may comprise different molecular structures and may be combined in ways that are obvious to those skilled in the art in the pertinent field. For instance, the block copolymer may have a biodegradable polymer as the central portion flanked by thermosensitive extensions and provided with cross-linkable moieties at both ends. Alternatively, the block copolymer may be branched with varying branching structures.

Thermosensitive Regions

In a preferred embodiment, the core thermosensitive oligomer or polymer can be a block copolymer of poly (ethylene oxide) (PEO) and poly(propylene oxide) (PPO). Most preferably, the oligomer or polymer may be a symmetrical block copolymer with three blockes with alternating PEO—PPO—PEO. The molecular formula can be written as

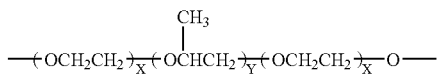

wherein X ranges from 1 to 300 and Y ranges from 1 to 300

Biodegradable Regions

"Biodegradable" means that the block copolymer can break down or degrade within the body of human or warm-blood animals to release the entrapped drug.

The biodegradable block co-polymer D is an oligerester or polyester, or is a random or block co-polyester or co-oligoester. The biodegradable moiety, a block co-polyester may comprise $(R_1)_m$ $(R_2)_n$ or $(R_3)_l$, wherein $R_1$, $R_2$ and $R_3$ are respectively

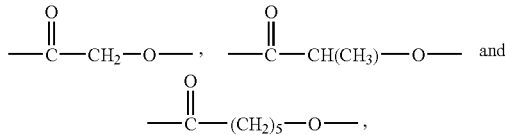

respectively, wherein m=0~100, n=0~100, l=0~100 with all of m, n and l not being zero simultaneously, although one or two of the three may be zero. The aliphatic polyester $R_1$ (or $R_2$ or $R_3$) or their copolymers are selected from the group(s) consisting of polymers or oligomers of d,l-lactic acid, l-lactic acid, glycolide, ε-caprolactone and alkyl substituted ε-caprolactone, and copolymers thereof.

Polymerizable Regions

Cross linking of the copolymer with crosslinkable ends are preferably formed via free radical polymerization, most preferably via a chemical initiator. The crosslinked moiety C can be expressed as

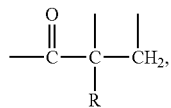

wherein R can be —H, —$CH_3$ or an alkyl. The preferred moiety with a crosslinkable group C* for further polymerization and is selected from the group consisting of acrylates, diacrylates, methacrylates, alkyl substituted acrylated, or other acrylic acid derivatives.

Macromer Synthesis

The ring-opening copolymerization of F and a lactone or an internal ester may be carried out under 0.1 mm Hg vacuum in the presence of a catalyst. The reaction temperature is in a range between 80~180° C., preferably 120~180° C., and most preferably 140~160° C. The reaction time is over 1 hour, usually in the range of 3~50 hours, preferably 15~24 hours. The catalyst is generally stannous octoate in an amount that is above 0.01 mole % per hydroxyl end group of F. Preferably, the amount of the catalyst is in the range of between 0.1 mole % to 5 mole %, most preferably from 0.5 mole %~1.5 mole %. The catalyst may also be selected from the group consisting of calcium hydride or zinc powder in a molar ratio of catalyst to hydroxyl end groups of F in the range of from 0.2/0.8 to 0.8/0.2, preferably ranging from 0.4/0.6 to 0.6/0.4. When the catalyst is calcium hydride or zinc powder, the reaction temperature is in the range of between 50~250° C., preferably 120~160° C. The reaction time is above 1 hour, preferably 3~50 hours. The molar ratio of F to the internal ester is in the range of from 0.1~99.9 to 99.9~0.1.

The resultant viscous material is dissolved with an organic solvent, such as dichloromethane, and then precipitated with an excess of anhydrous ether at a temperature in the range of −10~4° C. to remove the unreacted themosensitive oligomer or polymer F, the biodegradable moiety $R_1$ ($R_2$ or $R_3$ or their copolymers) and the residual catalyst. The product collected by filtration is then dried and preserved in a vacuum oven. The copolymer formed is then end-capped with acryloyl groups to form a polymerizable macromolecule. The molar ratio of acryloyl chloride or methyl acryloyl chloride or acryloyl chloride derivative to the hydroxyl end groups of F, or the hydroxyl end group of the copolymer of F and D, is generally in the range of from 1:1 to 100:1, preferably from 2:1 to 20:1.

A typical synthesis procedure is illustrated as follows: the copolymers of F and D are dissolved in dichloromethane or trichloromethane in a round-bottomed flask, and cooled to 0° C. in an ice bath. Triethylamine at the same molar amount as acryloyl chloride or its derivative is then added to the flask with stirring and a protective layer of dried nitrogen. Acryloyl chloride, methyl acryloyl chloride or a derivative of acryloyl chloride, is added dropwise to the mixture The reaction was carried out for 4~12 hours in the ice bath at a temperature in the range of 0~5° C., and then was maintained for 10~12 hours at room temperature of about 20° C. The reaction mixture was filtered to remove triethanolamine hydrochloride and then precipitated in excessive anhydrous ether. Finally, the macromer F(DC*)$_2$ is obtained by drying the precipitate collected by filtration in a vacuum oven.

Formation of Microgel

In one embodiment, the thermosensitive and biodegradable macromers (F(DC*)$_2$) are covalently cross-linked to form a microgel through inverse suspension polymerization. During the polymerization process, the macromer or a 1 wt %~49 wt % solution of the macromer is the dispersed or continuous medium. The concentration of the macromer solution ranges from 3 wt %~98 wt %. The solvent can be water, an aqueous solution, a hydrophilic solvent or a hydrophilic solution. The polymerization may be initiated using a water-soluble redox system with an oxidant, such as persulfate potassium or persulfate ammonium, or a reductant, such as a sulphite, hyposulphite or tetramethylethylenediamine (TEMED), where the latter is also used as an accelerator in the reaction. The amount of the initiating agent is above 0.001 wt % of the macromer, generally in the range of 0.01 wt %~8 wt %. The "initiating agent" refers to a single initiator, or a mixture of initiators, a co-catalyst or an accelerator. In some cases, it is advantageous to use a redox system for polymerization, because the associated free radical initiation may be triggered at a reasonable rate over a wide range of temperatures, and may even be triggered at low temperature of between 0–20° C.

Alternatively, polymerization may also be performed using thermal initiation, where the initiator is azoisobutyronitrile (AIBN) or benzoperoxide (BPO), etc.

During the process of polymerization, the continuous phase is generally a water-immiscible organic solvent selected from the group consisting of heptane, octane, cyclohexane, toluene, dimethylbenzene etc., and a mixture thereof. The dispersion phase is generally a hydrophilic solvent selected from the group consisting of water, an aqueous solution, a hydrophilic solvent, a hydrophilic solution, and a mixture thereof.

During the process of polymerization, the W/O nonionic emulsifier is added to the organic solvent. The emulsifier is selected from the group consisting of Span, Tween or their mixtures, at a weight ratio of between 100~50/0~50, preferably 100~80/0~20. Other nonionic emulsifier which can form a W/O emulsion may also be used.

During the polymerization process, the amount of emulsifier used ranges from 1 wt % to 40 wt %, preferably from 5 wt % to 15 wt %. The amount of the macromer in solution ranges from 1 wt % to 49 wt %, preferable from 7 wt % to 35 wt %. The reaction temperature is in the range of 20~100° C., generally 45~80° C. with a stirring speed is in the range from 60 to 2000 rpm. The speed of stirring may be constant or varied during the process. The reaction time is usually above 30 minutes, generally in the range of about 0.5~8 hours. The microgel formed is collected by filtration, washed several times with acetone and water, and then freeze dried or stored at a low temperature. The particle sizes of the microgel prepared in accordance with the present invention is from 5 nanometers to 5 millimeters.

During the process of polymerization, an initiator can be added to the flask of the macromer solution held in the bath set at the polymerization temperature. Since the polymerization temperature is usually above the phase transition temperature, the macromer solution might have physically gelated while the microgel particles are formed. This may result in the lack of well formed dispersed particles. In order to avoid physical gelation in the macromolecule solution before microparticle formation, the initiating agent can also be added into the flask together with macromolecule solution but at a lower temperature. The flask may then be heated to trigger polymerization only after the macromer solution has been well dispersed. The initiator can also be added in a different manner, for instance, as an initiator or accelerator solution into the continuous phase after the disperse phase of the macromer solution has formed.

The cross-linking may take place with a mixture of different macromers of the said (FDC*) structure.

The "particles" of "microgel" provided in accordance with the present invention can be stored in bulk or as a solvent mixture. The suitable solvent may be an aqueous or an organic solvent. Generally, water or an aqueous solution is used as the medium to swell the particles to form a hydrogel. The microgel particles formed in accordance with the present invention may be a xerogel, without a solvent or in a solvent. When the particles are in a hydrogel state, the solvent used is selected from the group consisting of distilled water, a buffer solution, a body fluid, a cell culture fluid, a tissue culture solution, or any other aqueous solution or solvent. The solvent used should not comprise an organic solvent as a major or principal part. The solvent may be a mixture.

It is understood that there might be some free ends in a chemically cross-linked network, wherein only one end of the chain is connected with an infinite cross-linked network. The macromolecule provided in the present invention can comprise 0~49 wt % of a block co-polymer with a double-bond at only one end of the molecule. Because of the possibility of the presence of some macromers with only a single crosslinkable end double bond, or less than 100% conversion of the double double-bond-ended macromers, it is inevitable and allowable for the microgel to comprise some dangling unpolymerized ends within the chemical gel network synthesized in accordance with the present invention. The chemically cross-linked network of the microgel of the present invention may comprise 0–49 wt % of structures with a dangling unpolymerizable end.

In the microgel provided by the present invention, the amount of the temperature-sensitive polymer or oligomer F comprising the principal part is in the range of 51 wt % to 99.9 wt %, while the biodegradable moiety or oligomer $R_1$ (or $R_2$ or $R_3$) or their copolymer is present in an amount in the range of 0.1 wt % to 49 wt %.

Drug Loading in the "Intelligent" Microgel

It is particularly advantageous that "intelligent" microgels are used for the controlled delivery of drugs, especially for bio-active agents such as proteins, including growth factors, etc. The term "intelligent" herein refers to a microgel that has a negative temperature sensitivity, i.e., the gel swells at a low temperature and contracts at a temperature that is above the "phase transition temperature" of the microgel. Such a temperature sensitivity at high temperature leads to "physical gellation" in this invention.

Conventional protein loading by in situ polymerization suffers from being conducted at a high temperature in the presence of organic solvents. These two conditions (organic solvent and high temperature) detrimentally affect the activity of the drug and sometimes even denature or degrade the protein drug. Moreover, when a drug solution is adsorbed into a conventional, known hydrogel, the amount of drug loaded is a serious limitation, in that a low loading level of less than 0.1 wt % is achieved according to Bromberg et al., (1998) *Adv. Drug. Deliv.* 31: 197–221).

A further problem is the difficulty of controlling the pore sizes in the microgel network, to permit the proteins to penetrate easily into the microgels and at the same time prevent the protein from leaching out from the microgel. To overcome these incompatible requirements, the principles governing chemical gelation and physical gelation have been taken into consideration together to develop the 'intelligent' microgels of the present invention. The incompatible requirements were solved by taking advantage of the intelligent design of a suitable material that has the desirable properties of a chemical gel and a physical gel.

Chemical gels are known to be permanent gels with covalently crosslinked infinite networks. The gelation process is not reversible in most of cases. Whereas, physical gels are formed due to a change in a physical parameter, such as a temperature change. In such cases, the process of gelation is usually reversible.

The microgels provided in the present invention are thermosensitive. They are chemical gels at a low temperature but are both chemical and physical gels simultaneously at a higher temperature, such as the body temperature. The particle sizes of the microgel change remarkably, i.e., the microgel particles shrink, when the temperature is higher than the phase transition temperature. In a gel with negative or reverse temperature sensitivity, a protein may be absorbed into the gel below the phase transition temperature.

When the temperature is raised over the phase transition temperature, the effective pore size of the gel network decreases and the protein absorbed therein are entrapped or kept in the microgel. In this case the network further gelates in response to a change in temperature. This is physical gelation causing the substance to be entrapped in the network.

Straightforward drying after absorbing the substance such as a drug is, of course, an alternative approach to keep the drug within the microgel. Drying after raising temperature following absorbing the drug at a low temperature is also necessary in storage of the drug-loaded microgels, as usual.

If the size of the protein is below the pore size of the microgel, the protein can enter relatively easily into microgel at a low temperature. When the microgel is heated to body temperature, the protein is entrapped in the microgel and is prevented from easily leaching out from the gel. It may be said that the protein molecules are entrapped within the microgel at the body temperature and thus may be released gradually.

The microgels of the present invention are biodegradable. The rate of degradation of the microgels of the present invention can be adjusted by selecting a suitable polyester or copolyester. The loaded protein or other adsorbed substance is thus released through diffusion and the degradation of the microgel.

The loaded substance may be any molecule or molecular mixture which does not react chemically with the microgel. A biologically active molecule is preferred, and may be any biomacromolecule or a derivative thereof. The solvent for biologically active molecules is usually water or an aqueous solution such as a PBS solution. The microgels of the present invention are particularly suitable for the controlled release of a protein, such as a growth factor.

In the present invention, the temperature sensitive macromer constitutes the principal part of the biodegradable microgel particles which might be used for loading the protein. It is contemplated that the microgels of the present invention are to be used not only for the controlled release of cell growth factors in tissue engineering, but may be a non-protein, a macromolecular drug or other material for which controlled release is desired.

The loaded microgels may be preserved at a low temperature or freeze dried and preserved at a low temperature. The activity of the loaded substance, particularly of a protein, can therefore be maintained easily and conveniently.

Compared with other carriers used in the controlled release of a drug, the biodegradable temperature-sensitive microgels provided in the present invention exhibit the following characteristics:

1. The hydrogel is in the form of an intelligent microgel and is biodegradable.
2. The microgel basically is composed of a synthetic polymer, principally a block copolymer with good biocompatibility.
3. The microgel provided in the present invention is prepared by inverse suspension polymerization from macromers comprising a thermosensitive central part linked with a biodegradable moiety, and polymerizable end(s).
4. The microgel provided in the present invention is temperature-sensitive. Because of this unique characteristic, a drug or an entrapped material, usually another macromolecular material, such as a protein, can be encapsulated AFTER the microgel has formed. So, during the drug loading process, the protein drug is not exposed to any organic solvents or a temperature that is higher than the human body temperature or that of a warm-blood animal.
5. In addition, because drug loading is performed after the microgel has formed, any residual starting material and/or initiator within the formed microgel can be thoroughly removed by washing to ensure the biocompatibility of the microgels.
6. The microgel is uncharged and is biodegradable primarily by hydrolysis. Thus, aside from pore size, there are no stringent selection requirements for the substance that is desired to be loaded. The encapsulation and release mechanism is universally applicable to any macromolecular drugs and may even be potentially useful for other substances that are to be applied in other areas beyond Pharmacology, where the controlled release of biologically active macromolecules and their derivatives is desired.
7. The sizes of the microgel particles of the present invention can be controlled by adjusting the stirring speed and the concentration of the emulsifier.
8. The microgels provided in the present invention possess the characteristics of both a chemically cross-linked gel and a physical gel. The phase transition temperature associated to physical gelation of the microgels of the present invention is adjustable by changing the ratio of the various macromers in the block co-polymer or other properties of the macromers, such as chain length, etc.
9. The effective pore size of the microgel network provided in accordance with the present invention can be controlled by selecting the molecular weight of the central block copolymer and by varying the amounts of the various components of the macromers or varying the macromer mixtures.
10. The degradation rate of microgel provided in the present invention is also controllable by selecting different polyesters to be co-polymerized with the temperature sensitive macromer, and by controlling their ratio in the copolymer. The degradation rate is generally not affected by the rate of gelation.
11. The microgels provided in accordance with the present invention are intelligent and biodegradable. Furthermore, the characteristics of the microgel, such as degradation rate, pore size, etc, can be adjusted independently. Consequently, the microgels of the present invention can be easily manipulated for desirable loading and release of various macromolecules. The technology is highly flexible and versatile.

The present invention will be further understood by reference to the following non-limiting examples.

EXAMPLES

Materials

PEO, PPO tri-block copolymers and stannous octoate were obtained from Sigma Aldrich; lactide, glycolide and caprolactone were obtained from PURAC and ACROS Organics respectively. Purification of ammonium persulphate and sodium bisulfite was carried out by the method of recrystallization. Dichloromethane was distilled prior to use.

Characterization

FTIR was carried out using Magna-550 instrument and 500 MHz proton was carried out using SF-500 instrument.

Example 1

Preparation of a Macromer

A 50 ml ampoule was flame dried under vacuum. 20 g of $PEO_{100}$-$PPO_{65}$-$PEO_{100}$ (the number in the subscript denotes the associated averaged degree of polymerization), 0.92 g of l-lactide and 1.3 ml of 10 mg/ml stannous octoate toluene solution were charged into the tube. After mixing the contents well, the tube was preheated to 60° C. for 6 hours under repeated cycles of vacuum and drying in argon or nitrogen to remove any volatile materials. The tube was then sealed off under vacuum (0.1 mmHg) and the mixture was copolymerized at 140° C. for 24 hours. The resultant copolymer was dissolved with dichloromethane, then precipitated with excess anhydrous ether (−10~0° C.), and recovered by filtration. The dried copolymer was then used for subsequent reactions. Other polymers were similarly synthesized using d,l-lactide or ε-caprolactone and calcium hydroxide in place of glycolide and stannous octoate and different PEO-PPO tri-block copolymers with different ratios of three components.

The above dried $PEO_{100}$-$PPO_{65}$-$PEO_{100}$-l-lactide copolymer was dissolved in dichloromethane in 250 ml round bottom flask. A ten fold molar excess, based on the molecular weight of the copolymer, of Triethylamine was added to the flask under the protection of dried nitrogen. Acryloyl chlorine in the same amount as triethylamine was added dropwise to the flask. The reaction mixture was stirred hours in an ice bath, followed by stirring for 12 hours or more at room temperature. After the reaction mixture was filtered to remove any insoluble triethylamine salt, the macromolecule was obtained by pouring the filtrate into a large excess of anhydrous ether (−10~0° C.) and recovering the precipitate by further filtration. Finally, the precipitate was dried in vacuum oven for two or three days. The macromer obtained was called ($PEO_{100}$-$PPO_{65}$-$PEO_{100}$)-$LA_4$-DA ($LA_4$ denotes that there are, on average, about 4 lactic-acid repeating units on each end of the block copolymer based upon the feed molar ratio; DA denotes di-acryloyl groups, namely, each acryloyl group at one end).

Production of Microgels Using a REDOX Initiating System

Inverse suspension polymerization reactions were performed in a 250 ml four-neck flask, fitted with a reflux condenser and a mechanical Teflon stirrer and under an inert atmosphere of nitrogen. The continuous phase comprised 200 ml of heptane and an emulsifier Span 60, in an amount of 4 wt % of heptane. The disperse phase was 10 ml of 20% w/w of the macromolecule, with ammonium persulphate and TEMED. After the flask was heated to 60° C. using an oil bath, the aqueous disperse phase was added dropwise at a rate of 1–2 drops per second into the flask. (3 wt % ammonium persulphate based on the amount of the macromolecule and 15 μl of the accelerator, TEMED were dissolved in the macromolecule solution 30 sec. before adding the disperse phase into the flask.)

The reaction was allowed to proceed for one hour at a stirring speed of 450 rpm. The resultant microgel was separated from the solvent with a standard sieve. The sieved microgel was washed firstly with acetone, followed by distilled water. After freeze drying, the particles sizes of the microgel obtained were in the range of 10–150 μm. When the microgel was allowed to swell in distilled water at 37° C., the particle sizes increased to 10–200 μm. The particle sizes further increased upon lowering of the temperature to 4° C. The morphology of the swollen microgel is shown in FIG. 2. The influence of temperature on the sizes of microgel particles was also investigated using a microscope provided with a device for controlling the temperature. The result is shown in FIG. 3, where the average volume or size of the microgel particles at 4° C. was taken as a control. The sizes of the microgel particles dropped sharply between 15° C. to 20° C.

Characterization of Macromers

An FTIR spectrum of the macromolecule was measured and calibrated. The strong absorption at 1730 $cm^{-1}$ demonstrates the presence of the lactide ester, the weak absorption at 1560 $cm^{-1}$ shows the presence of acrylic double bonds at the end groups.

A 500 MHz proton spectrum was recorded on an SF-500 instrument. The peaks at 1.13 ppm and 3.6 ppm reflect the presence of —$CH_3$ and —$CH_2$ in PPO and PEO respectively, and the peaks at 5.2 ppm and 1.4 ppm are attributable to the presence of —CH and —$CH_3$ in the lactic acid.

Example 2

The procedure employed is similar to that in Example 1. After a 50 ml ampoule was flame dried under vacuum, $PEO_{129}$-$PPO_{56}$-$PEO_{129}$, ε-carprolactone and stannous octoate were charged into the tube (the molar ratio of three components is 1:8:0.02). After the contents were well-mixed, the tube was preheated to 60° C. for 6 hours under repeated cycles of vacuuming and drying with argon or nitrogen to remove volatile materials. The tube was then sealed under vacuum (0.1 mmHg), and the mixture was copolymerized at 150° C. for 24 hours. Then the copolymer in dichloromethane was allowed to react with methylacryloyl chlorine and triethylamine. After filtration to remove solid materials, the filtrate was precipitated with excess anhydrous ether (−10~0° C.) and the precipitate was recovered by filtration and the dried macromolecular polymer obtained was the ($PEO_{129}$-$PPO_{56}$-$PEO_{129}$)-$CL_4$-DMA ($CL_4$ denotes that there are, on average, about 4 ε-carprolactone repeating units on each end of the block copolymer based upon the feed molar ratio; DMA denotes dimethylacryloyl groups, namely one methylacryloyl group at each end).

For the inverse suspension polymerization process, the continuous phase comprised dimethylbenzene and an emulsifier composed of Span 60 and Tween 80 in a weight ratio of 80:20. After the flask was heated to 80° C., a disperse phase of an aqueous solution of the ($PEO_{129}$-$PPO_{56}$-$PEO_{129}$)-$CL_4$-DMA macromers was added dropwise at a rate of 1–2 drops per second into the flask. The amount of the disperse phase was 6 wt % of the continuous phase. The reaction was carried out for half an hour at a stirring speed of 550 rpm. The microgel was separated from the liquid phase with a sieve and washed firstly with acetone, followed by distilled water. The sizes of the microgel particles ranged from 20–100 μm.

Example 3

The procedure used is similar to that described in Example 1. The macromer ($PEO_{103}$-$PPO_{39}$-$PEO_{103}$)-$LA_{16}$-DA was obtained by feeding $PEO_{103}$-$PPO_{39}$-$PEO_{103}$, 1-lactide and stannous octoate in a molar ratio of 1:16:0.02 before di-acryloylated. For the inverse suspension polymerization process, the continuous phase comprises heptane and an emulsifier composed of Span 80 and Tween 80 in a weight ratio of 84:16. The amount of the emulsifier was 8 wt % of heptane. While the solution was stirred under nitrogen for 30 min in an ice bath, the aqueous disperse phase containing 15% w/w macromers was added dropwise at a rate of 1–2 drops per second into the flask. Then 3 wt % ammonium persulphate based on the macromer and 10 wt % sodium bisulfite based on the macromer were added into the flask. The amount of the disperse phase was 8 wt % of the continuous phase. After 30 min, the flask was heated to 50° C., and then held at this temperature for 1 hour at a stirring speed of 450 rpm. The microgel was separated from the mixture with a sieve. The sieved microgel was washed firstly with acetone, followed by distilled water. The resultant microgel particles were in the range of 20–150 μm.

Example 4

The procedure is similar to that in Example 1. The macromer $(PEO_{103}\text{-}PPO_{39}\text{-}PEO_{103})\text{-}(CL_4\text{-}LA_4)\text{-}DA$ was obtained by feeding $PEO_{103}\text{-}PPO_{39}\text{-}PEO_{103}$, ε-carprolactone, l-lactide and calcium hydroxide in a molar ratio of 1:8:4:2 followed by di-acryloylation. During the process of inverse suspension polymerization, the continuous phase comprised toluene and a mixed emulsifier (Span 80 and Tween 80 in weight ratio of 90:10). The amount of the emulsifier was 12 wt % of toluene. Then, 20 wt % of $(PEO_{103}\text{-}PPO_{39}\text{-}PEO_{103})\text{-}(CL_4\text{-}LA_4)\text{-}DA$ macromer in an aqueous solution was added dropwise at a rate of 1–2 drops per second into the flask. The suspension was stirred under nitrogen in an ice bath at a speed of 1000 rpm. The amount of the disperse phase was 10 wt % of the continuous phase. After 30 minutes, the flask was heated to 70° C. at a stirring speed of 360 rpm. Then a 3 wt % ammonium persulphate based on the macromolecule in 400 μl TEMED was added into the flask. The reaction was allowed to proceed for 1 hour. The microgel was separated from the reaction mixture with a sieve and washed with acetone and then by distilled water. The sizes of the microgel particles ranged from 30–150 μm.

Example 5

The continuous phase comprised heptane and an emulsifier Span 60, in an amount of 10 wt % heptane. After the flask was heated to 60° C. using a thermostatted oil bath, a mixture of 10 wt % of $(PEO_{100}\text{-}PPO_{65}\text{-}PEO_{100})\text{-}LA_8\text{-}DA$ and 13 wt % of $(PEO_{129}\text{-}PPO_{56}\text{-}PEO_{129})\text{-}CL_4\text{-}DA$ in aqueous solution was added dropwise at a rate of 1–2 drops per second into the flask. The disperse phase was 30 wt % of the continuous phase. The reaction was allowed to proceed for one hour with a stirring speed of 240 rpm. The microgel was separated with a sieve and washed firstly with acetone, followed by distilled water. After freeze drying, the sizes of the prepared microgel particles ranged from 20–150 μm.

Example 6

The procedure is similar to that in example 1. The macromer $(PEO_{100}\text{-}PPO_{65}\text{-}PEO_{100})\text{-}CL_8\text{-}DMA$ was obtained by feeding $PEO_{100}\text{-}PPO_{65}\text{-}PEO_{100}$, ε-carprolactone and stannous octoate in molar ratio of 1:16:0.2 followed by di-methyl acryloylation. During the inverse suspension polymerization process, the continuous phase comprised hexane and a mixed emulsifier (Span 80 and Tween 80 in weight ratio of 75:25) and AIBN (1 wt % of the macromer). The amount of the emulsifier was 8 wt % of hexane. Then, 20 wt % of the macromer $(PEO_{100}\text{-}PPO_{65}\text{-}PEO_{100})\text{-}CL_8\text{-}DMA$ in an aqueous solution was added dropwise at a rate of 1–2 drops per second into the flask. The amount of the disperse phase was 10 wt % of the continuous phase. The solution was stirred under nitrogen for 30 min in an ice bath, then the flask was heated to 60° C. with a stirring speed 400 rpm. The reaction was allowed to proceed for 4 hours. The microgel was separated with a sieve and washed with acetone and then distilled water. The sizes of the microgel particles ranged from 30–250 μm.

Biodegradability

Biodegradation of the microgels is essential for its use as a biomedical material. The rate of degradation also determines to a large extent the release rate of the loaded material. The biodegradation of the microgels in accordance with the present invention mainly takes place through the hydrolysis of the ester bond. FIG. 4 presents the hydrolysis data for two microgels in PBS at 37° C.

Example 7

Encapsulation and Release of a Protein (Bovine Serum Albumin)

2.8 ml of a 20 mg/ml Bovine serum albumin (BSA) aqueous solution was slowly added at 4° C. dropwise into 200 mg of a dried microgel prepared from the $(PEO_{100}\text{-}PPO_{65}\text{-}PEO_{100})\text{-}LA_8\text{-}DA$ macromer. Swelling took place for 48 hours at 4° C. followed by 24 hours at 37° C. The resultant loaded microgel was freeze dried.

The microgel loaded with the BSA protein was placed in a flask containing 40 ml of a phosphate-buffer solution (PBS, 0.1M, pH 7.4) and incubated at 37° C. At appropriate intervals shown in FIG. 5, 1.0 ml of the aqueous solution was collected and 1.0 ml of fresh PBS was added to the flask. The amount of BSA released was assayed by the Lowry method using an ultraviolet spectrophotometer. The release profile for BSA is shown in FIG. 5. The cumulative BSA released was 73% after 120 hr, from a drug loading level of 20 wt % of BSA in the microgel.

Example 8

Insulin Release Assay

Insulin was dissolved in PBS at a concentration of 20 mg/ml. Dry microgel was loaded by equilibration with an excess of the buffered solutions of insulin. The loaded microgels were placed in a flask containing 40 ml of PBS and incubated at 37° C. At appropriate intervals shown in FIG. 6, 1.0 ml of the aqueous PBS solution was collected and 1.0 ml of fresh PBS was added to the flask. The amount of insulin released was assayed by a Bradford method using an ultraviolet spectrophotometer. The release profile for Insulin is shown in FIG. 6.

Example 9

Toxicity of Microgels

The toxicity of the microgels described herein was evaluated by intramuscular injection of the $(PEO_{100}\text{-}PPO_{65}\text{-}PEO_{100})\text{-}LA_8\text{-}DA$ microgel in the skeletal muscle of SD rats.

The rats were purchased from the College of Medicine of Fudan University. The procedure used was as follows. Fifteen SD rats having an average weight of 250 g were divided into five groups. Each group consists of three rats. The test microgels were sterilized using alcohol aqueous solution in cell-culture room. After a sterilized microgel suspension of the microgel in physiological saline (20 mg/ml) was prepared, 0.5 ml of the suspension was injected into the skeletal muscle of each rat. Each rat received two injections. The injected microgels along with their surrounding tissues were retrieved by surgical incision after 1, 3, 5, 7, 9 days. The retrieved samples were processed for histological examination by paraffin embedment using hematoxylin and eosin (H & E) dye.

One-day after injection some inflammatory cells surrounding the tissues at the injection site were observed. However, there was no striking acute inflammatory reaction observed. After three days, the inflammatory cells almost disappeared. The microgel completely degraded and disappeared after 7 days.

It is obvious to those of skill in the art that modifications and variations can be made to the composition, the structure of the macromers, the methods of preparing the macromer and/or microgel, the resultant external shape and internal structure of the microgel, the ways to encapsulate and release the entrapped substances in the microparticles, based on the forgoing description. Such modifications and variations are intended to be within the scope of the following claims.

List of References
U.S. PATENT DOCUMENTS

| | | | | |
|---|---|---|---|---|
| 1. | 4,352,883 | October 1982 | Lim | 435/178 |
| 2. | 4,716,203 | December 1987 | Casey et al. | 525/408 |
| 3. | 5,986,043 | November 1999 | Hubbell et al. | 528/354 |
| 4. | 6,030,634 | Febraury 2000 | Wu et at. | 424/423 |
| 5. | 6,060,582 | September 2000 | Hubbell et al. | 528/354 |
| 6. | 6,129,761 | October 2000 | Hubbell et al. | 623/11 |
| 7. | 6,306,922 | October 2003 | Hubbell et al. | 522/71 |
| 8. | 6,541,033 | April 2003 | Shah | 424/486 |
| 9. | 0,099,709 | May 2003 | Shah et al. | 424/469 |

OTHER PUBLICATIONS

10. Baldwin S P., Saltzman W M., "Materials for Protein Delivery in Tissue Engineering," *Adv. Drug. Deliv. Rev.* 33: 71–86 (1998)

11. Blanco D., Alonso M J., "Protein Encapsulation and Release from Poly(lactide-co-glycolide) Microspheres: Effect of the Protein and Polymer Properties and of the Co-encapsulation of Surfactants," *Eur. J.Pharm. Biopharm.* 45: 285–294 (1998)

12. Bromberg L E., Ron E S., "Temperature-responsive Gels and Thermogelling Polymeric Matrices for Protein and Peptide Delivery," *Adv. Drug. Deliv. Rev.* 31: 197–221 (1998)

13. Cho K Y., Choi S H., Kim C H., Nam Y S., Park T G., Park J K., "Protein Release Microparticles Based on the Blend of Poly(d,l-lactic-co-glycolic acid) and Oligo-ethylene glycol Grafted Poly(l-lactide)," *J. Control. Release* 76: 275–284 (2001)

14. Cohen S., Yoshioka T., Lucarelli M., Hwang L H., Langer R., "Controlled Delivery Systems for Proteins Based on Poly(lactic/glycolic acid) Microspheres," *Pharm. Res.* 8: 713–720 (1991)

15. Fu J., Zhou R X., Fan C L., "Studies on the Syntheses and Properties of Poly(ester-anhydride)s for DDS," *Chemical Journal of Chinese Universities* 19(5): 813–816 (1998)

16. Fu J., Zhou R X., Fan C L., "Studies on the Syntheses and Drug Release Properties of Polyanhydrides Containing Phosphonoformic (or Acetic) Acid Ethyl Ester in the Main Chain," *Chemical Journal of Chinese Universities* 18(10): 1706–1710 (1997)

17. Jain R A., Rhodes C T., Railkar A M., Malick A W., Shal N H., "Controlled Release of Drugs from Injectable in Situ Formed Biodegradable PLGA Microspheres: Effect of Various Formulation Variables," *Eur. J. Pharm. Biopharm.* 50: 257–262 (2000)

18. Jeong B., Bae Y H., Lee D S., Kim S W., "Biodegradable Block Copolymers as Injectable Drug-delivery Systems," *Nature* 388: 860–862 (1997)

19. Langer R., "Drug Delivery and Targeting," *Nature* 392: 5–10 (1998)

20. Lanza R P., Langer R., Vacanti J., "Principles of Tissue Engineering ($2^{nd}$ Ed.), Academic Press, New York, 2000

21. Li M X., Zhuo R X., Qu F Q., "Synthesis and Characterization of Novel Biodegradable Poly(ester amide) with Ether Linkage in the Backbone Chain," *J. Polym. Sci. part A: Polym. Chem.* 40(24): 4550–4555 (2002)

22. Sawhney A S., Hubbell J A., "Rapidly Degraded Teroplymers of dl-lactide, glycolide, and ε-caprolactone with Increased Hydrophilicity and Copolymerization with Polyethers," *J Biomed. Mater. Res.* 24(10): 1397–1411 (1990)

23. Sawhney A S., Pathak C P., Hubbell J A., "Bioerodible Hydrogels Based on Photopolymerized Poly(ethyleneglycol)-co-poly(α-hydroxy acid) Diacrylate Macromers," *Macromolecules* 26: 581–587 (1993)

24. Singh M., Shirley B., Bajwa K., Samara E. Hora M., O'Hagan D., "Controlled Release of Recombinant Insulin-like Growth Factor from a Novel Formulation of Polylactide-co-glycolide Microparticles," *J. Control. Release* 70: 21–28 (2001)

25. Wu C., Zhou S Q., "Thermodynamically Stable Globule State of a Single Poly(N-isopropylacrylamide) Chain in Water," *Macromolecules* 28(15): 5388–5390 (1995)

26. Wu C., Zhou S Q., "Internal Motions of Both Poly(N-isopropylacrylamide) Linear Chains and Spherical Microgel Particles in Water," *Macromolecules* 29(5):1574–1578 (1996)

27. Yasuhiko T., "The Importance of Drug Delivery Systems in Tissue Engineering," *Pharmaceutical Science & Technology Today* 3: 80–89 (2000)

28. Zentner G M., Rathi R., Shin C., McRea J C., Seo M H., Oh H., Rhee B G., Mestecky J., Moldoveanu Z., Morgan M., and Weitman S., "Biodegradable Block Copolymers for Delivery of Proteins and Water-insoluble Drugs," *J. Control. Release* 72: 203–215 (2001)

29. Zhuo R X., Li W., "Preparation and Characterization of Macroporous Poly(N-isopropylacrylamide) Hydrogels for the Controlled Release of Proteins," *J. Polym. Sci. part A: Polym. Chem.* 41(1): 152–159 (2003)

30. Zhu Z X., Xiong C D., Zhang L L., Yuan M L., Deng X M., "Preparation of Biodegradable Polylactide-co-poly (ethylene glycol) Copolymer by Lactide Reacted Poly (ethylene glycol)", *Eur. Polym. J.* 35: 1821–1828 (1999)

We claim:

1. A method of preparing a thermosensitive and biodegradable microgel wherein
    a) the microgel has a chemically cross-linked network comprising at least one negative temperature-sensitive macromolecule and one biodegradable group represented by structural formula:

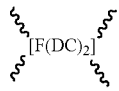

wherein

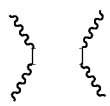

represents chemical cross-linked bonds;
  $F(DC)_2$ represents a polymeric chain between the cross-linked bonds; F is a temperature-sensitive block copolymer of poly(ethylene oxide) (PEO) and poly (propylene oxide) (PPO); D is a biodegradable moiety; and C is a cross-linked moiety
  b) the microgel is in the form of microparticles prepared by the following steps:
    i) co-polymerizing a biocompatible polymer or oligomer F with an internal ester D by ring opening polymerization of D in the presence of F using a catalyst; wherein F is a temperature-sensitive polymer or oligomer; D is a biodegradable moiety;
    ii) end capping the copolymer with a crosslinkable moiety C to provide a macromer with crosslinkable ends;
    iii) cross linking the crosslinkable end(s) of the macromer to form the microparticles of the microgel by inverse suspension polymerization, wherein the continuous phase is a water-insoluble organic solvent and the dispersion phase consists of a hydrophilic medium in which the macromer is present,
  c. the microgel is useful for encapsulating a drug post polymerization; and
  d. the drug encapsulated microgel is injectable into the body.

2. The method of claim 1, wherein the temperature-sensitive polymer or oligomer F is a tri-block copolymer of poly(ethylene oxide) (PEO) and poly(propylene oxide) (PPO), having the formula

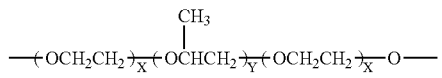

wherein X is from 1 to 300, Y from 1 to 300.

3. The method of claim 1, wherein D is a biodegradable oligoester or polyester, or is a biodegradable random or block co-oligoester or co-polyester selected from the group consisting of $(R_1)_m$, $(R_2)_n$, and $(R_3)_l$, wherein $R_1$, $R_2$, and $R_3$ respectively are represented by:

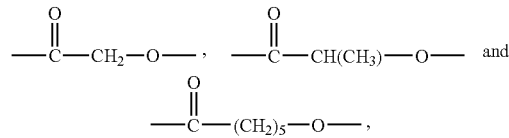

wherein m=0~100, n=0~100, l=0~100, and not all of m, n and l can be zero.

4. The method of claim 1, wherein the cross-linked moiety C is

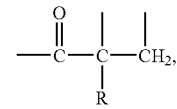

wherein R can be —H, —$CH_3$ or alkyl.

5. The method of claim 1, wherein the temperature-sensitive polymer or oligomer F is used as the principal constituent in an amount based on the microgel in the range of 51 wt %~99.9 wt %.

6. The method of claim 1, wherein the chemically cross-linked network is obtained by crosslinking a mixture of different block copolymers, F and D and comprising a crosslinked moiety C.

7. The method of claim 1, wherein 0 wt %~49 wt % of the chemically cross-linked network comprises a dangling unpolymerized end.

8. The method of claim 1, wherein the size of the microgel particles is in the range of 5 nm to 5 mm.

9. The method of claim 1, wherein the microgel is in a bulk state or admixed with a solvent.

* * * * *